United States Patent [19]

Rattner

[11] Patent Number: 5,766,138
[45] Date of Patent: Jun. 16, 1998

[54] THERAPY APPARATUS WITH SIMPLE SETTING OF A DESIRED DISTANCE FROM A REFERENCE POINT

[75] Inventor: Manfred Rattner, Grossenseebach, Germany

[73] Assignee: Siemens Aktiengesellschaft, Munich, Germany

[21] Appl. No.: 819,835

[22] Filed: Mar. 18, 1997

[30] Foreign Application Priority Data

Apr. 18, 1996 [DE] Germany ................. 196 15 344.1
Dec. 5, 1996 [DE] Germany ................. 196 50 552.6

[51] Int. Cl.[6] .................................................. A61B 17/22
[52] U.S. Cl. .................................................. 601/4
[58] Field of Search ........................ 600/439; 601/2–4

[56] References Cited

U.S. PATENT DOCUMENTS

| | | |
|---|---|---|
| 4,697,588 | 10/1987 | Reichenberger . |
| 4,811,725 | 3/1989 | Grasser ................. 601/4 |
| 4,928,672 | 5/1990 | Grasser et al. . |
| 4,986,275 | 1/1991 | Ishida et al. ................. 600/439 |
| 5,005,580 | 4/1991 | Okazaki . |
| 5,095,907 | 3/1992 | Kudo et al. . |
| 5,165,412 | 11/1992 | Okazaki . |
| 5,285,772 | 2/1994 | Rattner . |
| 5,443,069 | 8/1995 | Schaetzle ................. 601/2 |

Primary Examiner—Brian Casler
Attorney, Agent, or Firm—Hill & Simpson

[57] ABSTRACT

A therapy apparatus has a source of acoustic waves which propagate through a medium in the source, a setting arrangement by means of which a desired distance can be set between a body surface of a patient and a reference point of the source, and an arrangement for determination of the distance of the body surface of the patient from the reference point. The latter arrangement includes a sensor element that is contained inside the source and which can be displaced in the direction of the acoustic axis of the source. The sensor element is in at least indirect contact with body surface of the patient during the determination of the distance. The apparatus also has a display arrangement for providing a quantitative visual indication of the distance.

10 Claims, 5 Drawing Sheets

THERAPY APPARATUS WITH SIMPLE SETTING OF A DESIRED DISTANCE FROM A REFERENCE POINT

BACKGROUND OF THE INVENTION

1. Field of the Invention

The present invention is directed to a therapy apparatus of the type having a source of acoustic waves and an acoustic propagation medium, with setting means for setting a desired distance between the source and a body region of a patient, and with means for determining the distance between the source and the body region of the patient.

2. Description of the Prior Art

Therapy apparatuses of the above type are used, for example, in the treatment of patients suffering from a kidney stone, whereby the kidney stone is generally disintegrated under the effect of focused acoustic waves. For the treatment of the patient, it is important to set the distance between the source of acoustic waves and a body region of the patient, e.g. the surface of the body, in such a way that the focus zone of the acoustic waves comes to lie substantially on the kidney stone to be disintegrated, in order to avoid damage to healthy tissue by the focused acoustic waves. For this purpose, the therapy apparatuses of the type described above contain setting means and means for determining the distance between the body region of the patient and the source, which is usually an ultrasound location unit.

Therapy apparatuses of this type are known for example from German OS 39 13 023 and from European Application 445 322, which include an ultrasound location unit that is housed in the source of acoustic waves and that can be moved in the direction of the acoustic axis of the source.

In the reference U.S. Pat. No. 5,095,907, a therapy apparatus is described that has a rod that can be moved in the direction of the acoustic axis, with an ultrasound location unit arranged on the rod. In order to set the focus position of the source of acoustic waves, the volume of the acoustic propagation medium in the source of acoustic waves is changed.

In certain forms of therapy, e.g. pain therapy using focused acoustic waves, lower demands of precision are made in the setting and determination of distances between the source of acoustic waves and the body region of the patient to be treated, since in this form of therapy, there is a fairly low risk of damage to healthy tissue by the focused acoustic waves. For cost reasons, means for determining the distance between the body region of the patient and the source are foregone, which, however, is not advisable under all circumstances.

SUMMARY OF THE INVENTION

An object of the present invention is to provide a therapy apparatus of the type described above with which the distance from the source to a body surface of a patient to be treated can be determined and set simply and economically.

According to the invention, this object is achieved in a therapy apparatus having a source of acoustic waves with an acoustic of propagation medium, with setting means for setting a desired distance between a body surface of a patient and a reference point of the source, with means for determining the distance of the body surface of the patient from the reference point, containing a sensor element that is housed inside the source and can be displaced in the direction of the acoustic axis of the source. The element touches the body surface of the patient at least indirectly during the determination of the distance. Display means are provided for the quantitative display of the distance. After the physician has oriented the source of acoustic waves relative to a body region to be treated such that the acoustic axis of the source runs at least approximately through the body region to be treated, the physician can thus set the required distance of the reference point of the source from the body surface of the patient by applying the sensor element to the body surface. This element thus is positioned relative to the source corresponding to the respectively desired distance. The sensor element can lie directly or indirectly on the bodily surface of the patient, e.g. via a coupling membrane of the source. For setting the desired distance of the reference point of the source from the body surface of the patient, a display unit provides a quantitative display of the current value of the distance. The physician can thus set the desired distance of the reference point of the source from the bodily surface quickly and surely on the basis of the quantitative distance values displayed using the display unit.

In a preferred embodiment of the invention, measurement means are allocated to the sensor element for determining the distance of the region of the sensor element provided for application to the body surface from the reference point, the measurement means preferably containing a position transmitter. The position transmitter provides a signal by means of which the current distance of the region of the sensor element applied to the body surface of the patient to the reference point of the source can be quantitatively determined. The sensor element can be displaced in a simple fashion in the direction of the acoustic axis of the source, manually or automatically.

In a further embodiment of the invention measurement means in the form of a calibrated scale are used. The scale is preferably arranged on the sensor element, and is graduated in such a way that when the sensor element is applied directly or indirectly to the body surface of the patient, the distance of the reference point of the source from the body surface can, for example, be read directly on the scale by a physician. The scale can be provided as the sole measurement means for the determination of the distance, or can be provided in addition to the position transmitter.

In another version of the invention, the sensor element, which is preferably a tube closed at one end, is constructed so that it can be removed from the region of the source of acoustic waves that houses the sensor element. This enables the optional use of other means, e.g. an optical positioning unit.

According to a further embodiment of the invention, the setting means include a control and computing unit and means for optionally suppling and removing acoustic propagation medium to or, respectively, from the source of acoustic waves. The means for supply and removal of acoustic propagation medium to or from the source of acoustic waves include a supply container for the acoustic propagation medium, hose pipes, at least one inlet/outlet sleeve, and at least one pump. Using the setting means, acoustic propagation medium can optionally be supplied to or removed from a chamber of the source of acoustic waves that houses the acoustic propagation medium, the source being applied to the body of the patient via a flexible elastic coupling membrane that seals the chamber in a liquid-tight fashion, for the purpose of introducing acoustic waves into the body of the patient. In this way, the source can be moved away from the body of the patient or moved toward the body of the patient, so that the focal zone of the acoustic waves comes to be located in the body region to be treated. Using the display means, the actual value and target value of the distance of the reference point of the source from the body surface of the patient can thus be continuously monitored.

In a further embodiment of the invention the display means for the quantitative display of the distance of the reference point of the source from the body surface of the patient can be a monitor on which the respective current distance is quantitatively displayed. In this way, the setting of the distance can be easily monitored and controlled.

According to a variant of the invention, the display means additionally include or are exclusively formed by a pointer. The pointer thereby works together with the scale, which is preferably arranged on the jacket surface of the tube, in such a way that the tip of the pointer pointing to the scale indicates quantitatively the distance of the body surface of the patient from the pointer functioning as a reference point, with the tube being applied directly or indirectly to the body surface of the patient. This embodiment of the invention is practically economical, since electronic measurement and display means for the quantitative determination or display of the distance are not needed.

DESCRIPTION OF THE PREFERRED EMBODIMENTS

Figure 1:
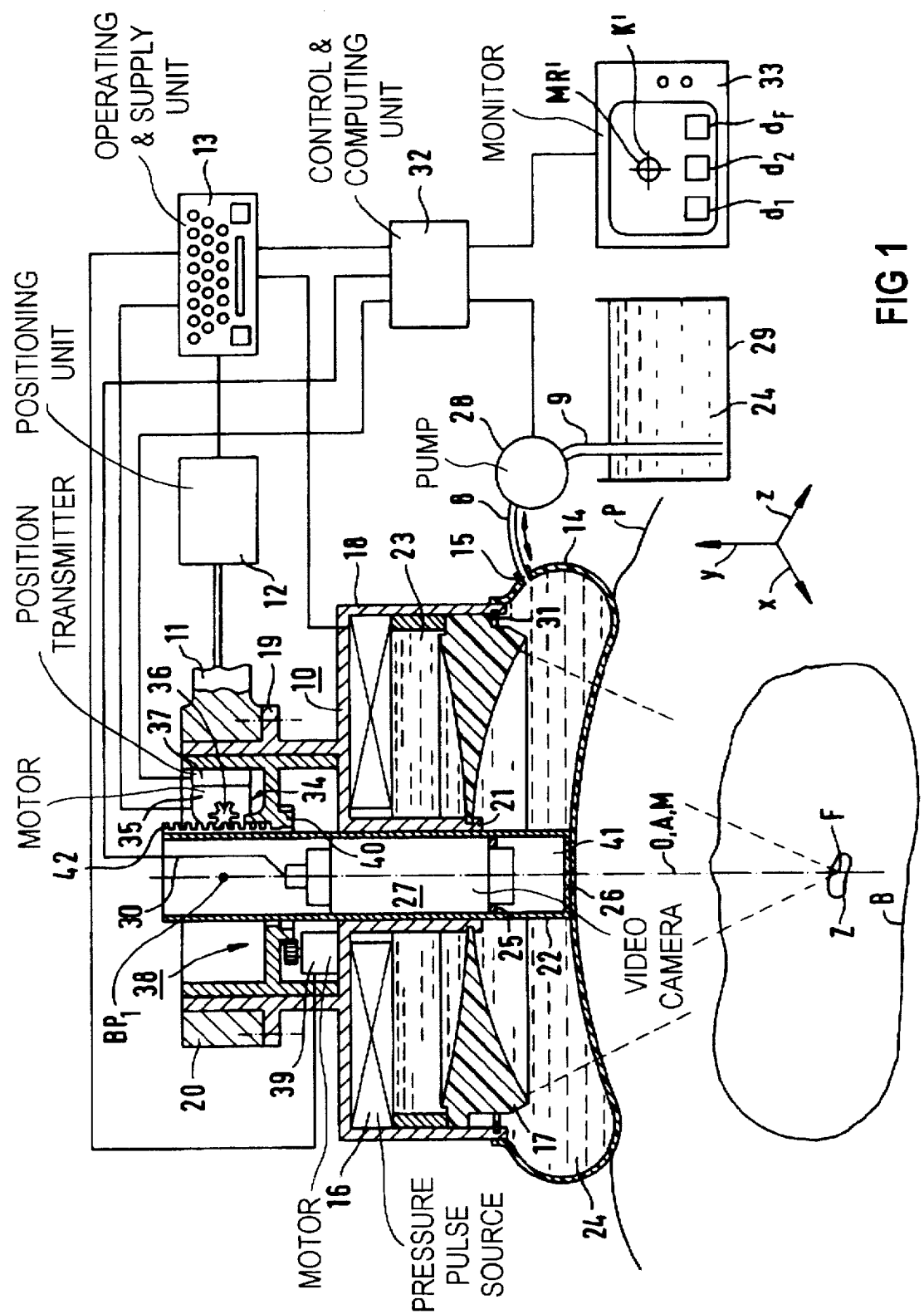
FIG. 1 illustrates an inventive therapy apparatus in a partly sectional, partly block-type representation.

As shown in FIG. 1, the inventive therapy apparatus has a source of focused acoustic waves, generally designated 10, attached via a support 11 to a positioning unit 12, which is indicated only schematically. This positioning unit 12 allows displacement of the source 10 in the direction of the axes x, y, z of the spatial coordinate system indicated in FIG. 1. An operating and supply unit 13 is connected to the displacement unit 12, the operating and supply unit 13 containing all the components required for the operation of the source 10, and is provided with a keyboard for the operation of the therapy apparatus. The source 10 contains a central light-transparent region (described in more detail below) and is applied to the body surface of a patient P with a likewise light-transparent coupling membrane 14, so that focused acoustic waves produced during the operation of the therapy apparatus can be introduced into the body of the patient P, who is for example suffering from pain in a body region B.

As can be seen in FIG. 1, the source 10 of focused acoustic waves contains an electromagnetic pressure pulse source 16 (not shown in more detail) and an acoustic focusing lens 17. The focusing lens 17 focuses the pressure pulses emitted by the pressure pulse source 16 to a focus F, which in practice is a spatial (three-dimensional) focus zone. The focus F lies on the acoustic axis A of the source 10, corresponding to the middle axis M of the source 10, the source 10 being fashioned with approximate rotational symmetry relative to the axis M. The pressure pulse source 16 and the focusing lens 17 are housed in a housing 18, which is sealed in a liquid-tight manner at its end remove from the pressure pulse source 16 by means of the elastic, flexible coupling membrane 14. The pressure pulse source 16 is, for example, an electromagnetic pressure pulse source, as described with respect to design and function in European Application 0 188 750 and European Application 0 301 630. The high-voltage pulse generator required for the operation of the pressure impulse source 16 is a component of the operating and supply unit 13, to which the pressure pulse source 16 is connected via a corresponding line.

At its other end, adjacent to the pressure impulse source 16, the housing 18 has a mounting flange 19 that serves to fasten the source 10 to a mounting ring 20 of the support 11 by means of screws in FIG. 1 only the center lines of two such screws are indicated with broken lines.

The spaces located between the pressure impulse source 16 and the focusing lens 17, and between the focusing lens 17 and the coupling membrane 14, are filled with an acoustic propagation medium. In the case of the present exemplary embodiment, both spaces contain the same acoustic propagation medium, namely water 23 and 24. The two spaces filled with water 23 and 24 are separated from one another in the case of the present exemplary embodiment by the focusing lens 17, however, they can be connected with one another, in particular if both spaces contain the same acoustic medium of propagation.

The focusing lens 17 is a biconcavely shaped lens of solid material, fashioned from a material, e.g. polystyrene, in which the speed of propagation of sound is greater than in the water 23 and 24 provided as an acoustic propagation medium. The lens 17 is held in the housing 18 by a mounting ring 31.

The coupling ring 14 has an opening 15 in the form of a sleeve. A hose conduit 8 connects the sleeve 15 of the coupling membrane 14 with a pump 28, the pump 28 being in turn connected via a hose conduit 9 with a supply container 29, which is partly filled with the acoustic propagation medium, i.e., water 24. The pump 28 can be operated so that, as needed, water 24 can be pumped into the space between the focusing lens 17 and the coupling membrane 14, while water 24 can be pumped out of the space between the focusing lens 17 and the coupling membrane 14. In this way, the volume of the space between the focusing lens 17 and the elastic and flexible coupling membrane 14 can be optionally increased or reduced.

A cup-like tube 22 (i.e., a tube closed at one end) is set into an opening 41 of a cylindrically tubular inner wall 21 of the housing 18. The tube 22 is fashioned, at least in the region of its base 226 from a material transparent to light, e.g. Plexiglas®. The tube 22 can be displaced axially in the opening 41 of the inner wall 21 and is contained therein in a liquid-tight fashion. Sealant, not shown in FIG. 1, can possibly be provided for this purpose. A video camera 27 (not shown in more detail in FIG. 1) is set into the tube 22 at a certain distance from the base 26 thereof. The optical axis 0 of the video camera 27 coincides with the acoustic axis A of the source 10. The focal length of the lens of the video camera 27 can be set via a control and computing unit 32, which is connected to the video camera 27 by means of a video signal line 30. In addition, the video camera lens is surrounded by an annular light source 25, in order to obtain usable video exposures in conditions of insufficient incoming light. The base 26 of the tube 22 is also provided with an optical mark that lies on the acoustic axis A of the source 10.

In the present exemplary embodiment, the control and computing unit 32 is a commercially available PC, to which a monitor 33 and a keyboard (not shown in FIG. 1) are connected.

The central opening 41 of the source 10 inside the inner wall 21, in which opening the tube 22 is located, represents the above-mentioned region transparent to light, from which the water 24 is excluded by means of the tube 22 in order to avoid negative influences on the image quality. For this purpose, when the source 10 is applied to the body surface of the patient P indicated in FIG. 1, the tube 22 is pushed into the opening 41 of the inner wall 21 until its base 26 lies against the bodily surface of the patient P, with the interposition of the coupling membrane 14. For this purpose, a further positioning unit 34 is provided by means of which the tube 22 can be displaced in the axial direction. The positioning unit 34 contains an electromotor 35 provided with a pinion 36, which engages a rack 42 provided on the tube 22. A position transmitter 37 is allocated to the positioning unit 34, the transmitter 37 supplying a signal corresponding to the axial position of the tube 22 to the control and computing unit 32. According to this signal, the distance $d_1$ (see FIG. 2) of the base 26 of the tube 22 from a reference point $BP_1$ lying on the acoustic axis A of the source 10 is quantitatively determined by the control and computing unit 32. The distance $d_F$ of the focus F from the reference point $BP_1$ of the source 10 is stored in the operating and supply unit 13 of the source 10, and is provided via a control line of the control and computing unit 32.

The tube 22 can additionally be rotated about the acoustic axis A by means of a displacement unit 38. The displacement unit 38 contains an electromotor 39 provided with a pinion, which engages a toothed ring 40, contained in the housing 18 and connected to the tube 22 to co-rotation therewith. The rack 42 extends into a groove of a carrier 40a for the ring 40. The connection between the carrier 40a and the tube 22, such as by engaging keys and key ways, allows the tube 22 to be displaceable along the axis A while still being co-rotatable with the carrier 40a.

The electromotors 35 and 39 of the positioning units 34 and 38 are connected with the operating and supply unit 13 via corresponding lines.

For the treatment of the patient, the patient is first positioned in a suitable position on a treatment table (not shown). The treating physician first scans the body region indicated by the patient as the locus of the pain, and marks the point on the body surface of the patient under which, according to the patient, the center Z of the pain is located, e.g. with a cross (not shown in FIGS. 1 and 2). Next, the patient P is oriented on the treatment table such that the region of the body surface marked with a cross is located approximately in the region of the acoustic axis A of the source 10. On the basis of the video signals from the video camera 27, which are displayed on the monitor 33 connected to the control and computing unit 32, the treating physician can orient the source 10 with the operating and supply unit 13 so that the image K' of the cross made by the physician on the body surface of the patient P and the image MR' of the optical mark of the base 26 of the tube 22 coincide on the monitor 33. The acoustic axis A of the source 10 then runs through the cross, and at least approximately also through the pain center Z of the patient P.

In order to position the focus F of the source 10 so that its distance from the bodily surface is at least approximately equal to the distance of the pain center Z from the bodily surface, the physician proceeds as follows:

By means e.g. of an estimate or using ultrasound diagnosis, the physician determines the distance $d_2$ of the pain center Z from the body surface of the patient P, which distance remains at least approximately constant during the treatment, and enters the distance $d_2$ via the keyboard of the operating and supply unit 13 of the therapy apparatus, so that the distance $d_2$ is known to the control and computing unit 32. By changing the distance $d_1$ of the reference point $BP_1$ from the body surface of the patient P, or from the base 26 of the tube 22, which is thereby applied to the bodily surface of the patient P, the physician subsequently sets the distance of the focus F of the source 10 from the body surface so that it corresponds to the distance $d_2$ of the pain center Z from the body surface. For this purpose, the current distance values $d_1$, $d_2$ and dF according to FIG. 2 are quantitatively displayed (e.g. in units of centimeters) next to the video images from the video camera 27, but generally as a rule only the distance $d_1$ is changed.

Figure 2:
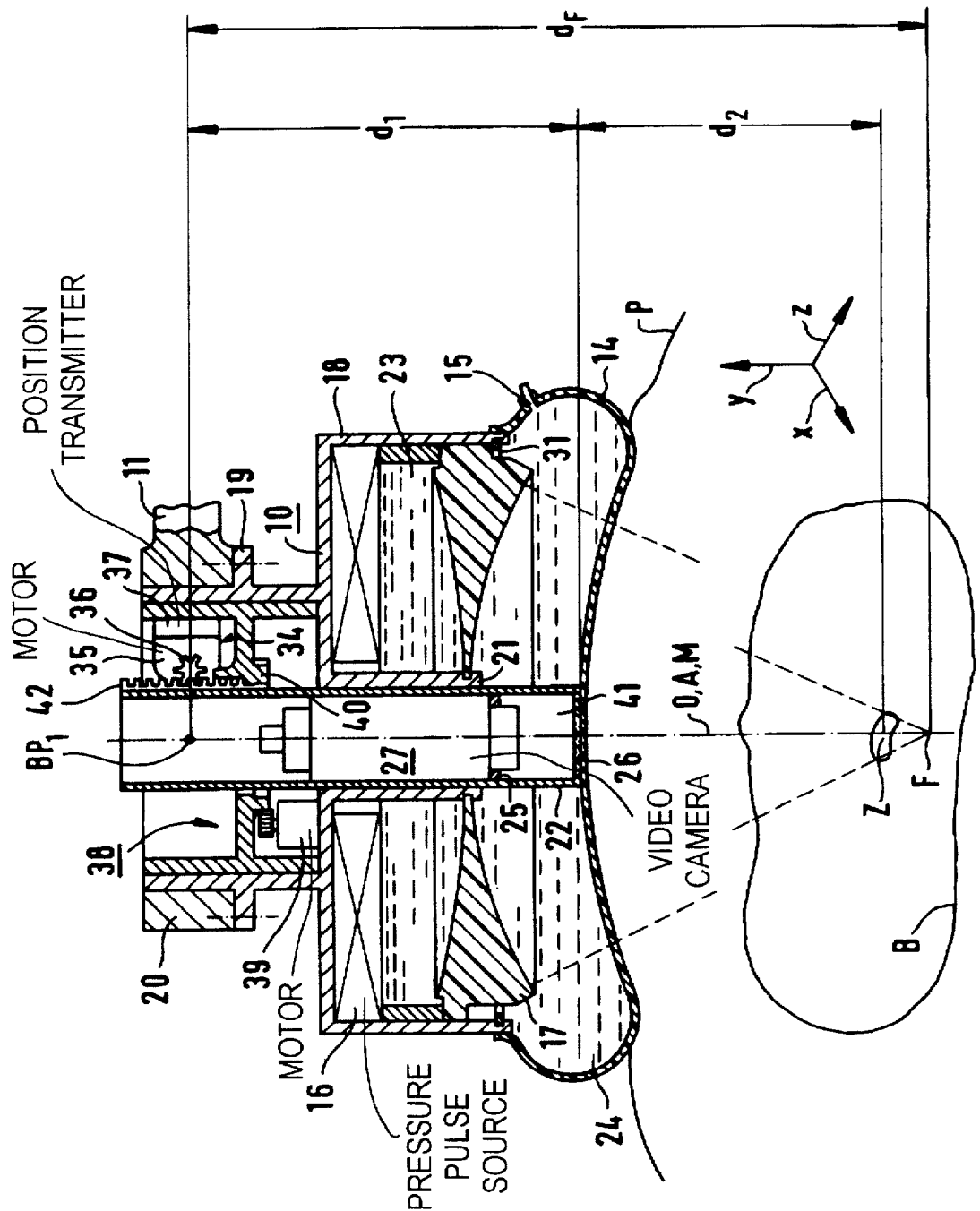
FIG. 2 illustrates the therapy apparatus according to FIG. 1, in a partly sectional representation with distance indications.

If, as in the present exemplary embodiment according to FIG. 2, the focus F of the source 10 comes to lie behind the pain center Z of the patient, the distance $d_1$ must be increased until the sum of the distances $d_1$ and $d_2$ is equal to the distance $d_F$. If this is the case, the focus F of the pressure impulses is located in the pain center Z of the patient. During the setting of the position of the focus, the pump 28 is driven by the control and computing unit 32 so that it pumps water 24 from the supply container 29 into the space between the focusing lens 17 and the coupling membrane 14 via the hose conduits 8 and 9, causing the volume of this space to increase, and the source 10 moves away from the body surface. At the same time, the tube 22 is led into the cylindrically tubular inner wall 21 of the housing 18 via the positioning unit 34, possibly limited by the force in effect between the tube 22 and the body surface, in such a way that its base 26 always lies snugly on the body surface of the patient P. The control and computing unit 32 is thus provided at all times with a signal via the position transmitter 37, from which signal the unit quantitatively determines the current distance $d_1$ and displays it on the monitor 33. The pumping process remains active until, by means of the introduction of water 24 into the space between the focusing lens 17 and the coupling membrane 14, the source 10 has been moved far enough away from the body surface by the increase in volume of the space so that the sum of the distances $d_1$ and $d_2$ is equal to the distance $d_F$. The physician can thereby follow the increase of the distance $d_1$ on the monitor. If the sum of the distances is identical, a corresponding visual signal is emitted to the monitor 33.

If, after positioning the source 10 over the pain center Z of the patient P, the focus F of the source 10 lies in front of the pain center Z of the patient P, then in this case water is pumped out of the space between the focusing lens 17 and the coupling membrane 14 into the supply container 29, so that the volume of the space between the focusing lens 17 and the coupling membrane 14 becomes smaller and the focus F of the source 10 moves toward the pain center Z of the patient. The tube 22 is thereby again steadily guided in order to determine the distance $d_1$. The distance $d_1$ of the body surface of the patient P, or of the base 26 of the tube 22, from the reference point $BP_1$ steadily becomes smaller in this case, until the sum of the distances $d_1$ and $d_2$ is again identical with the distance $d_F$ of the focus F from the reference point $BP_1$ of the source 10.

If, in the manner specified, the images K' and MR' of the cross and of the mark on the base 26 of the tube 22 are made to coincide, and the required distance of the focus F from the body surface is set, then, with the cooperation of the patient, the physician shifts the source 10 relative to the body of the patient P while carefully transmitting focused acoustic waves of reduced intensity until the focus F is actually located in the pain center Z. The actual treatment can now begin.

Figure 3:
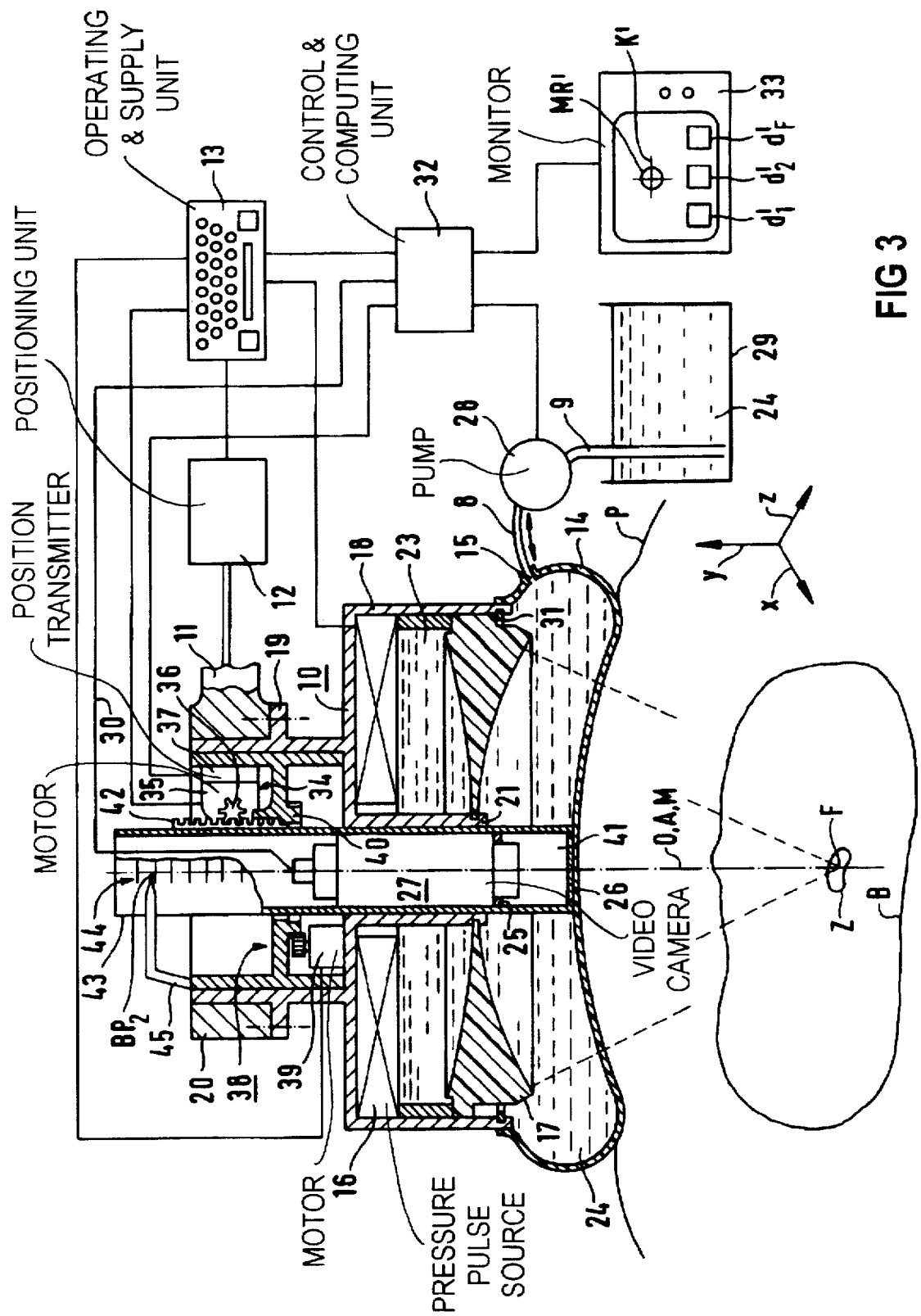
FIG. 3 illustrates a further embodiment of the inventive therapy apparatus in a partly sectional, partly block-type representation.

FIG. 3 illustrates a further embodiment of the inventive therapy apparatus that is largely identical to the therapy apparatus shown in FIG. 1 in its construction and functioning. Identical components of the two embodiments are also provided with the same reference characters.

The therapy apparatus according to FIG. 3 has a cup-like tube 43, of substantially the same construction as the tube 22 of the therapy apparatus according to FIG. 1, which, however, is provided with a graduated scale 44 on its outer jacket surface. Like the tube 22, the tube 43 is set into the opening 41 of the cylindrically tubular inner wall 21 of the housing 18 of the source 10, and is constructed at least in the area of its base from a material transparent to light, e.g. Plexiglas®. At a certain distance from its base, it supports the video camera 27, for recording image information from the body surface of the patient P. Moreover, the tube 43, like the tube 22, has an optical mark on its base that lies on the acoustic axis A of the source 10.

The scale 44, which has units of centimeters in the present exemplary embodiment, operates together with a pointer 45 attached to the displacement unit 38, the tip of the pointer 45 representing the reference point $BP_2$ of the source 10 in the therapy apparatus according to FIG. 3. If the tube 43 is applied to the body surface of the patient P, the current distance $d_1'$ (see FIG. 4) of the reference point BP of the source 10 from the body surface of the patient P, or from the base of the tube 43 which is lying on the bodily surface, can be read on the basis of the scale 44 and the tip of the pointer 45.

During the treatment of the region B to be treated of the patient using the therapy apparatus according to FIG. 3, the physician first proceeds in the same way as in the treatment of the region B of the patient P with the therapy apparatus according to FIG. 1, i.e. the physician positions the patient P on a treatment table (not shown) and directs the acoustic wave source 10 onto the body region B of the patient P to be treated in the way previously specified. The acoustic axis A of the source 10 then again runs through the cross, which has been brought to coincide with the optical mark on the base of the tube 43, and (at least approximately) with the pain center Z of the patient P.

The physician subsequently again positions the focus F of the source 10 such that its distance from the body surface is at least approximately equal to the distance of the pain center Z from the body surface.

Figure 4:
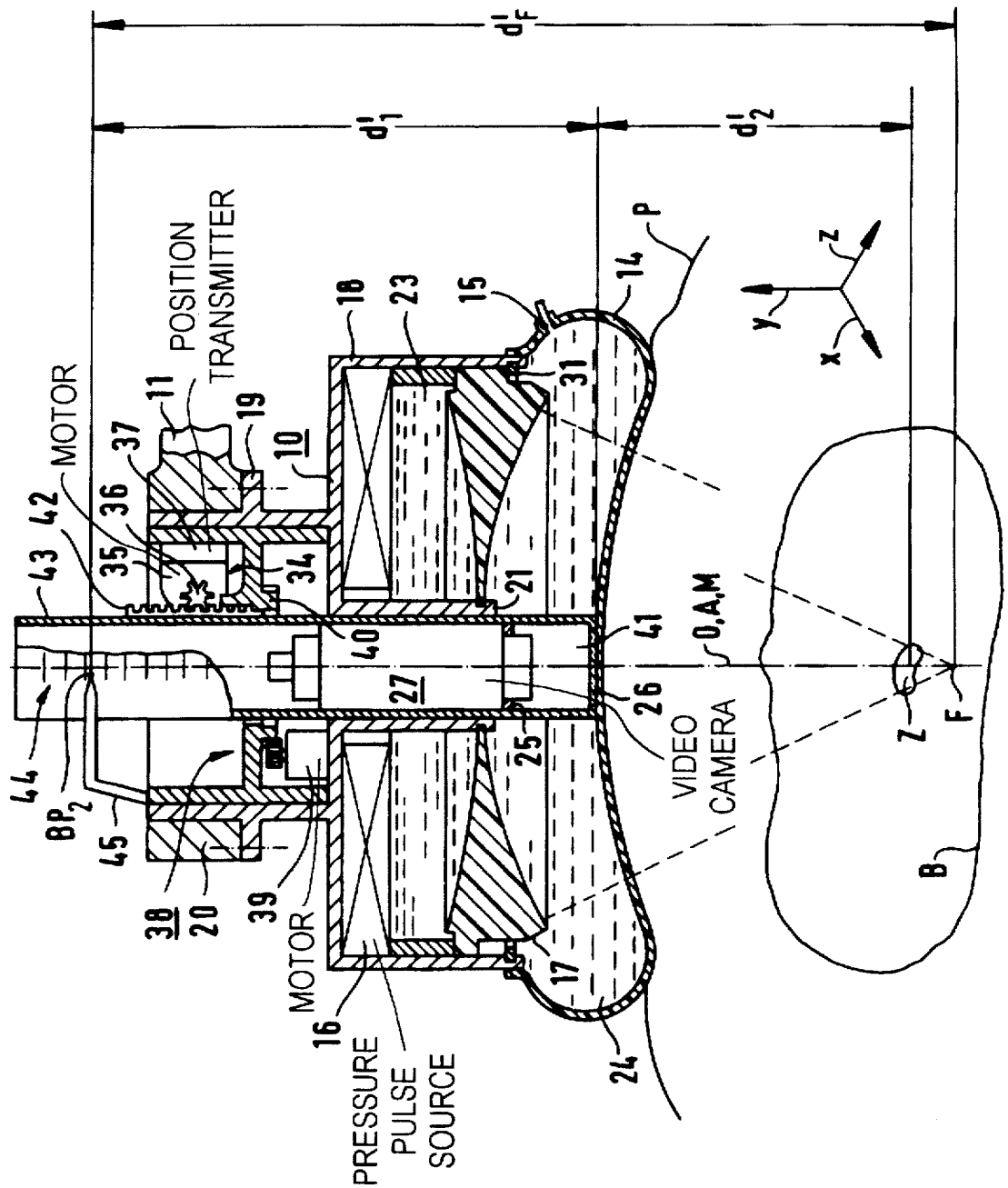
FIG. 4 illustrates the therapy apparatus according to FIG. 3 in a partly sectional representation with distance indications.

If, as illustrated in FIG. 4, the distance $d_F'$ of the focus F from the reference point $BP_2$ is known to the physician due to the use of a focusing lens 17 with a fixed focal length, and the distance $d_2'$ is known through an estimate or through ultrasound diagnosis, then from the difference of the distance values $d_F'$ and $d_2'$ the physician can easily calculate the distance of the reference point $BP_2$ of the source 10 from the body surface, which distance is to be set for positioning the focus zone on the pain center Z of the patient P. Subsequently, by placing the tube 43 on the body surface of the patient P, the physician can easily shift the focus F of the source 10 to the pain center Z of the patient by means of the current distance $d_1'$, read from the scale 44. By continuous visual monitoring of the scale 44, and thus of the current distance $d_1'$, and according to the position of the focus zone in front of or behind the pain center Z of the patient P, the physician thereby uses the operating and supply unit 13 to control the supply or removal of water 24 into or out of the source 10. In the present exemplary embodiment, in which the focus F lies behind the pain center Z of the patient P (cf. FIG. 4), water 24 is supplied to the source 10 in order to shift the focus F. The focus F of the source 10 thereby shifts along the acoustic axis A in the direction toward the pain center Z of the patient P. For the quantitative display of the current distance value $d_1'$ on the basis of the pointer 45 and the scale 44, the tube 43 must be guided so that it always lies snugly on the bodily surface of the patient P. If the calculated distance value is set, i.e. is indicated on the scale 44, the focus F is substantially oriented to the pain center Z of the patient P.

If the images K' and MR' of the cross and of the mark on the base of the tube 43 are thus brought into coincidence, as in treatment using the therapy apparatus according to FIG. 1, and the required distance of the focus F from the bodily surface is set, then with the cooperation of the patient P the physician again carefully shifts the source 10 relative to the body of the patient P, while transmitting focused acoustic waves of reduced intensity, until the focus F is actually located in the pain center Z. The actual treatment can now begin.

Moreover, in the embodiment of the therapy apparatus according to FIG. 3 the respective current distance values $d_1'$, $d_2'$ and $d_F'$ can additionally be displayed on the monitor 33. The display can be omitted, however, in which case the position transmitter 37 can also be omitted (the transmitter providing a signal corresponding to the axial position of the tube 43, by the spacing of the base of the tube 43 from the reference point $BP_2$ can be quantitatively determined).

Figure 5:
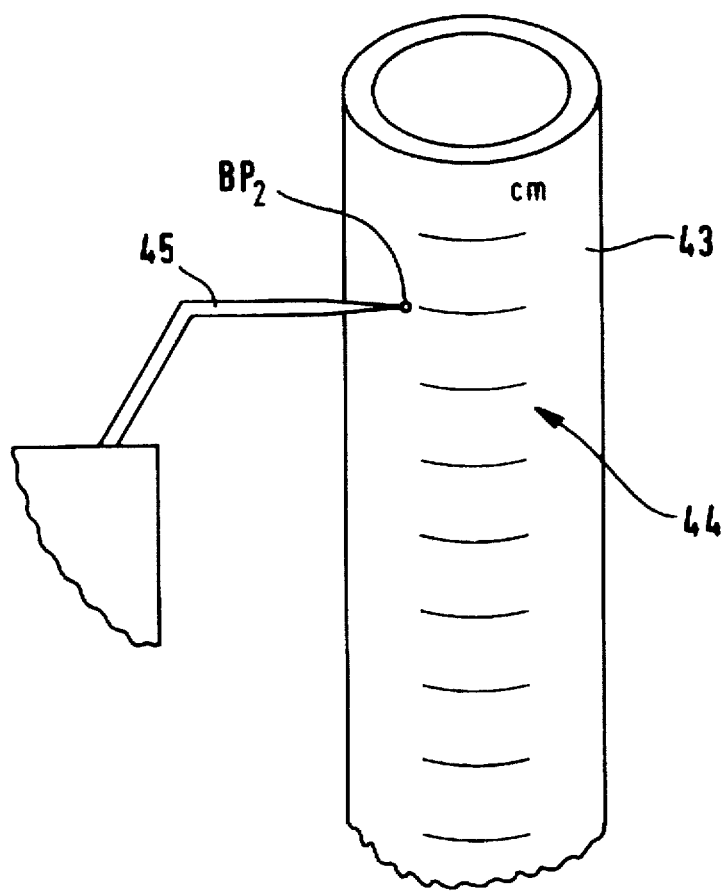
FIG. 5 illustrates a detail of the therapy apparatus according to FIG. 3.

FIG. 5 again illustrates, in a detail representation, the tube 43 with the scale 44 in centimeters, with the pointer 45 of the therapy apparatus according to FIG. 3, the pointer 45 functioning as a reference point $BP_2$.

The scale 44 does not necessarily have to use centimeters as units, but rather can just as usefully employ a different unit.

The optical mark on the base 26 of the tube 22 or on the base of the tube 43 is, moreover, not required if a mark identifying the position of the acoustic axis A is electronically mixed into the video image, in a known manner.

In the specified exemplary embodiment, the tube 22 or the tube 43, and therewith the video camera 27, is displaced in the opening 41 of the inner wall 21 of the housing 18 around the acoustic axis A by means of the positioning unit 38, and is displaced in the direction of the acoustic axis A by means of the positioning unit 34. The tube 22 or the tube 43, and therewith the video camera 27, however, can be manually shifted around the acoustic axis A or along the acoustic axis A. The possibility of rotating the tube 22 or the tube 43 around the acoustic axis A can also be omitted, since it is not absolutely required in order to bring the images K' of the cross and MR' of the mark on the base 26 of the tube 22 or on the base of the tube 43 into coincidence.

Furthermore, the video camera 27 can be connected directly to a television monitor. In this case, the position transmitter 37, if present, is connected to the operating and supply unit 13 of the source 10, which carries out the distance calculations and correspondingly controls the pump 28.

In the specified exemplary embodiment, the focusing lens 17 has a fixed focal length, however, it is also possible to use a variable-focus lens, i.e. one with an adjustable focal length.

The tube 22 or the tube 43 can, moreover, be removed from the source 10 of acoustic waves if necessary, but it must be ensured that a corresponding tube is introduced into the source 10 in a way not shown, in order to prevent the loss of water 24.

Moreover, the tube 22 or the tube 43 need not necessarily be of a cup-like construction, but rather can, in particular, be of semicircular construction at the base. However, under certain circumstances precautionary measures must then be taken to ensure that there are no negative influences on the quality of the video images.

The coupling membrane 14 need not necessarily be provided with only one sleeve 15 for the supply and removal of water 24 and with only one pump 28. Rather, for the supply and removal of water into the space between the focusing lens 17 and the coupling membrane 14, several pumps, sleeves, hose conduits and, if necessary, valves that prevent backflow of the water, can be provided.

If the two water-filled spaces 23 and 24 of the source 10 are not, as in the present exemplary embodiment, separated from one another by the focusing lens 17, the housing 18 of the source 10 can be provided with corresponding supply and removal sleeves in the region of the space between the pressure pulse source 16 and the focusing lens 17, via which sleeves water 23 or 24 is supplied or removed for increasing or reducing the volume of the space between the focusing lens 17 and the coupling membrane 14.

In the present exemplary embodiment, the source 10 contains an electromagnetic pressure pulse source, however, the inventive therapy apparatus can alternatively contain another type of pressure pulse source, for example one that operates piezoelectrically. Moreover, it is possible to provide another source of acoustic waves, e.g. an ultrasound source that produces ultrasound in the form of continuous sound, ultrasound bursts or ultrasound pulses, in place of a pressure pulse source.

Furthermore, it is possible to manually carry out the orientation of the source 10 over the bodily region of the patient P marked with a cross by the physician, rather than by means of the operating and supply unit 13.

The positioning of the source 10 of acoustic waves using the video camera 27 is also not required. It is possible either to introduce a simple light-transparent tube that can be displaced in the direction of the acoustic axis A into the opening 41 of the inner wall 21 of the source 10, so that the physician can, by direct observation orient the acoustic axis A of the source 10 at least approximately to the cross by applying the base of the tube to the bodily surface of the patient P via the coupling membrane 14, or to omit the light-transparent region entirely. In the latter case, the positioning of the source relative to the patient's body such that its acoustic axis runs through the region to be treated must take place exclusively with the cooperation of the patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy apparatus comprising:

a source of acoustic waves containing an acoustic propagation medium through which acoustic waves emitted by said source propagate along an acoustic axis toward a patient, said source having a reference point therein;

setting means for setting a selected distance between a body surface of a patient to be treated by said acoustic waves and said reference point, said setting means including means for determining said distance between said body surface of the patient and said reference point, said means for determining the distance including a sensor element disposed inside said source and means for displacing said sensor element in directions along said acoustic axis of said source, said sensor element adapted to at least indirectly come into contact with said surface of the patient for determining said distance; and indicator means for providing a visual quantitative indication of said distance.

2. A therapy apparatus as claimed in claim 1 further comprising means allocated to said sensor element for measuring said distance between said body surface of the patient and said reference point.

3. A therapy apparatus as claimed in claim 2 wherein said measuring means comprise a position transmitter.

4. A therapy apparatus as claimed in claim 2 wherein said measuring means comprise a graduated scale.

5. A therapy apparatus as claimed in claim 4 wherein said source further comprising a housing and wherein said indicator means comprise a pointer mounted stationary in said housing past which said graduated scale is moved as said sensor element is displaced.

6. A therapy apparatus as claimed in claim 1 comprising means for removably mounting said sensor element in said source of acoustic waves.

7. A therapy apparatus as claimed in claim 1 wherein said sensor element comprises a tube closed at an end closest to said patient.

8. A therapy apparatus as claimed in claim 1 wherein said setting means include control means for operating said means for displacing dependent on operator-entered commands, and means for selectively supplying and removing acoustic propagation medium into and out of said source for positioning a region of action of said acoustic waves inside said patient.

9. A therapy apparatus as claimed in claim 8 wherein said means for selectively supplying and removing acoustic propagation medium comprise a supply container having at least one sleeve through which said acoustic propagation medium flows, and a pump which pumps said acoustic propagation medium between said supply container and said source.

10. A therapy apparatus as claimed in claim 1 wherein said indicator means comprise a monitor.

* * * * *